United States Patent
Thomann et al.

(10) Patent No.: US 8,791,319 B2
(45) Date of Patent: Jul. 29, 2014

(54) LAMINATE ABSORBENT CORE FOR USE IN ABSORBENT ARTICLES

(75) Inventors: Maike Thomann, Kriftel (DE); Bruno Johannes Ehrnsperger, Bad Soden (DE); Alessandra Massa, Caramanico Terne (IT); Manuel Laso, Madrid (ES); Birgit Wirtz, Köln (DE); Roland Engel, Sulzbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 133 days.

(21) Appl. No.: 13/492,229

(22) Filed: Jun. 8, 2012

(65) Prior Publication Data

US 2012/0316525 A1 Dec. 13, 2012

(30) Foreign Application Priority Data

Jun. 10, 2011 (EP) .................................... 11169514

(51) Int. Cl.
*A61F 13/15* (2006.01)
(52) U.S. Cl.
USPC ........... 604/367; 604/370; 604/374; 604/368; 604/366; 604/378; 604/375

(58) Field of Classification Search
USPC .......... 604/370, 367, 374, 368, 366, 375, 378
See application file for complete search history.

(56) References Cited

U.S. PATENT DOCUMENTS

| | | |
|---|---|---|
| 6,790,798 B1 | 9/2004 | Suzuki et al. |
| 2008/0312617 A1 | 12/2008 | Hundorf et al. |
| 2009/0270826 A1 | 10/2009 | Schafer et al. |
| 2009/0312738 A1 | 12/2009 | Lavon et al. |

FOREIGN PATENT DOCUMENTS

EP 0875224 11/1998

OTHER PUBLICATIONS

International Search Report, PCT/US2012/041100, mailed Aug. 7, 2012, 12 pages.

*Primary Examiner* — Jacqueline F. Stephens
(74) *Attorney, Agent, or Firm* — Laura L. Whitmer

(57) ABSTRACT

The invention relates to absorbent cores having high amounts of superabsorbent polymer material which are immobilized by adhesive. The absorbent cores have reduced peak force when subjected to the Laminate Compression Extension Test Method and also exhibit reduced delamination upon swelling of the superabsorbent polymer material.

14 Claims, 6 Drawing Sheets

LAMINATE ABSORBENT CORE FOR USE IN ABSORBENT ARTICLES

CROSS REFERENCE TO RELATED APPLICATION

This application claims priority to European Patent Convention Application No. 11169514.4, filed Jun. 10, 2011, the substance of which is incorporated herein by reference.

FIELD OF THE INVENTION

In one aspect, the invention relates to absorbent cores having high amounts of superabsorbent polymer material which are immobilized by adhesive. The absorbent cores have reduced peak force when subjected to the Laminate Compression Extension Test Method and also exhibit reduced delamination upon swelling of the superabsorbent polymer material.

BACKGROUND OF THE INVENTION

The use of superabsorbent polymer material in disposable absorbent articles, such as disposable diapers, is well known. The use of superabsorbent polymer material facilitates absorbent articles having a thinner absorbent core versus the use of absorbent materials such as fluff pulp (also referred to as airfelt), especially while the absorbent article is in the dry state.

In absorbent cores having a high percentage of superabsorbent polymer material and little or no airfelt (cellulose fibers) the superabsorbent polymer material is often sandwiched between carrier substrates. The carrier substrates are typically nonwoven webs. The superabsorbent polymer material needs to be immobilized between the carrier substrates to ensure that the superabsorbent polymer material does not migrate within the absorbent core. Such immobilization is important both when the absorbent core is in the dry state as well as in use, when the absorbent core gets wetted with liquids, such as urine. Immobilization of the superabsorbent polymer material is often done with adhesives, such as hot melt adhesives. It is known to immobilize the superabsorbent polymer material (which is typically in the form of superabsorbent polymer particles) by applying adhesive in form of a fibrous network. The superabsorbent polymer material is thus adhered to the carrier substrates as well as to each other. However, there is still a need for improved immobilization of the superabsorbent polymer material to ensure that expansion of the superabsorbent polymer materials upon liquid absorption is not unduly restricted by the adhesive.

There is also a need for improved immobilization of the superabsorbent polymer material to ensure that the expanded core upon liquid absorption does not delaminate which might result in reduced superabsorbent polymer material immobilization and overall reduced integrity of the absorbent core.

SUMMARY OF THE INVENTION

The invention relates to a laminate absorbent core comprising a first and second carrier substrate, and superabsorbent polymer particles placed between the first and second carrier substrate. The superabsorbent polymer particles are immobilized by a first adhesive, the superabsorbent polymer particles making up more than 90%, or more than 95%, or more than 98% by weight of the total amount of material comprised between the first and second carrier substrates. The absorbent core has a peak swelling restriction pressure of from 50 N/m² to 400 N/m², a swelling restriction pressure at 20 mm of more than 30 N/m², and a ratio of peak swelling restriction pressure to swelling restriction pressure at 20 mm of from 1 to 8 when subjected to the Laminate Compression Extension Test described herein.

DETAILED DESCRIPTION OF THE INVENTION

Definitions

Figure 1:
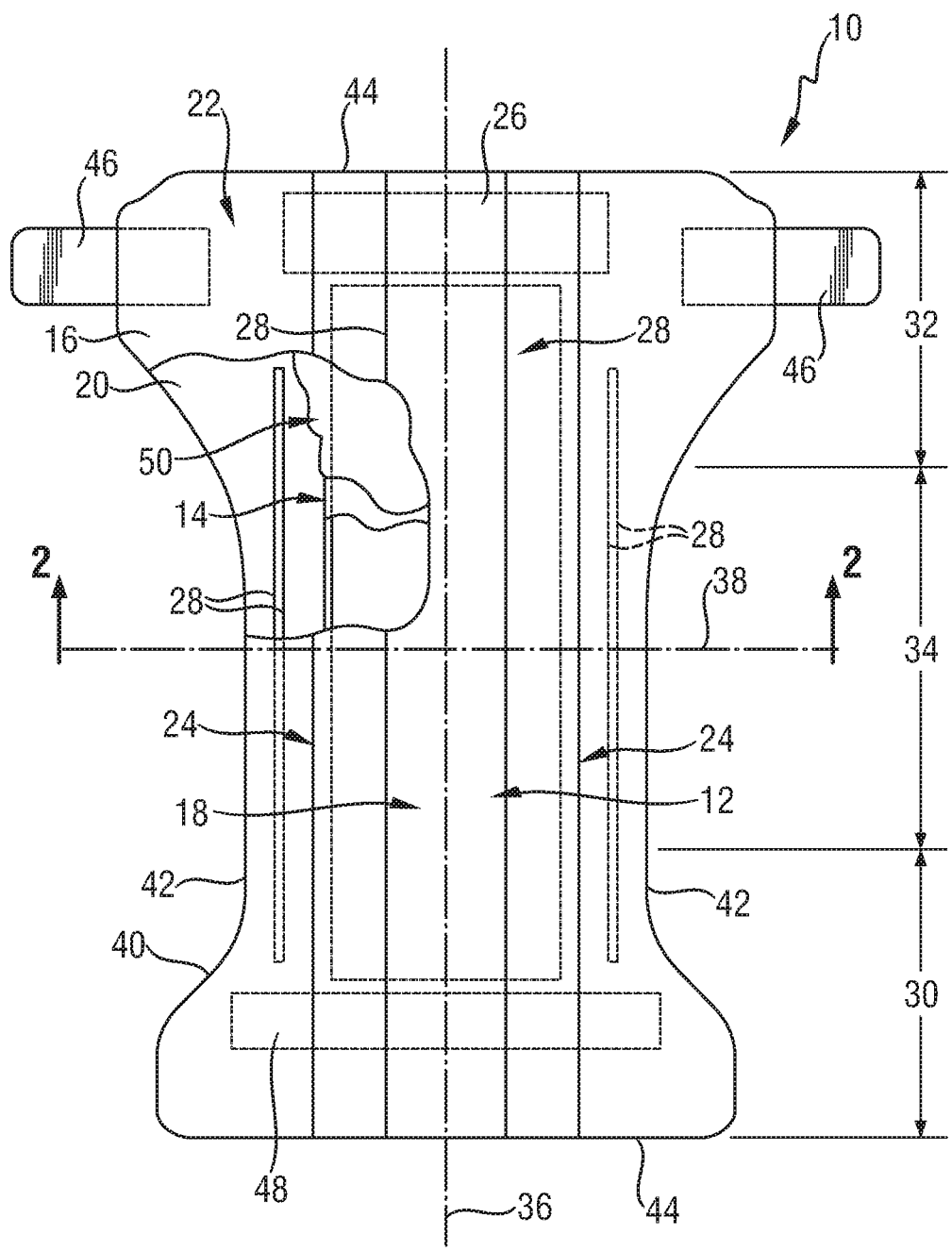
FIG. 1 is a plan view of a schematic drawing of a disposable diaper in accordance with an embodiment of the invention

"Absorbent article" refers to devices that absorb and contain body exudates, and, more specifically, refers to devices that are placed against or in proximity to the body of the wearer to absorb and contain the various exudates discharged from the body. Absorbent articles may include diapers, pants, training pants, adult incontinence undergarments, sanitary napkin, and the like. As used herein, the term "body fluids" or "body exudates" includes, but is not limited to, urine, blood, vaginal discharges, breast milk, sweat and fecal matter. Preferred absorbent articles of the invention are diapers, pants, training pants and/or sanitary napkins.

"Absorbent core" means a structure that may be disposed between a topsheet and backsheet of an absorbent article for absorbing and containing liquid received by the absorbent article.

"Airfelt" is used herein to refer to comminuted wood pulp, which is a form of cellulose fibers (absorbent fibers).

"Diaper" refers to an absorbent article generally worn by infants and incontinent persons about the lower torso so as to encircle the waist and legs of the wearer and which is specifically adapted to receive and contain urinary and fecal waste.

"Diaper-pant", as used herein, refers to disposable garments having a waist opening and leg openings designed for infant or adult wearers. A diaper-pant may be placed in position on the wearer by inserting the wearer's legs into the leg openings and sliding the pant into position about a wearer's lower torso. A diaper-pant may be preformed by any suitable technique including, but not limited to, joining together portions of the article using refastenable and/or non-refastenable bonds (e.g., seam, weld, adhesive, cohesive bond, fastener, etc.). A diaper-pant may be preformed anywhere along the circumference of the article (e.g., side fastened, front waist fastened). The terms "diaper-pant" is also commonly referred to as "prefastened diaper," "pull-on diaper," "training pant," and "pant".

"Disposable" is used in its ordinary sense to mean an article that is disposed or discarded after a limited number of usage events over varying lengths of time, for example, less than 10 events, less than 5 events, or less than 2 events. A disposable absorbent article is most often disposed after single use.

"Hot melt adhesive" as used herein refers to adhesives in alignment with the description given in "Adhesion and Adhesives Technology: An Introduction" by Alphonsus V. Pocius (Hanser publishers Munich, 1997). Therein a hot melt is defined as an adhesive applied from the melt and gaining strength upon solidification.

"Laminate absorbent core" as used herein refers to an absorbent core comprising a first and second carrier substrate, and superabsorbent polymer material placed between the first and second carrier substrate, wherein the superabsorbent polymer material is immobilized by a first adhesive.

A "nonwoven web" is a manufactured sheet, web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments, and twisted bundles of continuous filaments (yarn). Nonwoven webs can be formed by many processes such as meltblowing, spunbonding, solvent spinning, electrospinning, carding and airlaying. Nonwoven webs may be bonded by heat and/or pressure or may be adhesively bonded. Bonding may be limited to certain areas of the nonwoven web (point bonding). Nonwoven webs may also be hydro-entangled or needle-punched. The basis weight of nonwoven webs is usually expressed in grams per square meter ($g/m^2$).

"Superabsorbent polymer material" as used herein refers to substantially water-insoluble polymer particles that can absorb at least 5 times their weight of an aqueous 0.9% saline solution as measured using the Centrifuge Retention Capacity test (Edana 441.2-01). Preferred superabsorbent polymer materials are in the form of superabsorbent polymer particles.

"Superabsorbent polymer particles" is used herein to refer to an absorbent polymer material which is in particulate form so as to be flowable in the dry state.

Absorbent Article in the Form of a Diaper or Diaper-Pant

FIG. 1 is a plan view of a diaper 10 according to a certain embodiment of the invention. The diaper 10 is shown in its flat out, uncontracted state (i.e. without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis 12.

The chassis 12 of the diaper 10 in FIG. 1 comprises the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28 such as elastic strands.

One end portion of the diaper 10 is configured as a front waist region 30 of the diaper 10. An opposite end portion of the diaper 10 is configured as a back waist region 32 of the diaper 10. An intermediate portion of the diaper 10 is configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The diaper 10 may also include such other features as are known in the art including front and back ear panels, waist cap features, elastics and the like to provide better fit, containment and aesthetic characteristics.

In order to keep the diaper 10 in place about the wearer, at least a portion of the first waist region 30 may be attached by the fastening member 46 to at least a portion of the second waist region 32 to form leg opening(s) and an article waist. To this end, according to certain embodiments, the diaper 10 may be provided with a re-closable fastening system or may alternatively be provided in the form of a diaper-pant. When the absorbent article is a diaper, it may comprise a re-closable fastening system joined to the chassis for securing the diaper to a wearer. The fastening system may include at least one fastening member 46 and at least one landing zone 48. When the absorbent article is a diaper-pant, the article may comprise two side panels on each waist region 30, 32 joined to the chassis along the longitudinal edges of the side panels which face towards the longitudinal axis 36. The side panels of the front waist region 30 are further joined to the respective side panels of the back waist region 32 along their longitudinal edges facing away from the longitudinal axis 36 to form a pant.

Taking a cross section of FIG. 1 along the sectional line 2-2 of FIG. 1 and starting from the wearer facing side, the diaper 10 may comprise the topsheet 18, the components of the absorbent core 14, and the backsheet 20. Diaper 10 may also comprise an acquisition system 50 disposed between the liquid permeable topsheet 18 and the wearer facing side of the absorbent core 14. The acquisition system 50 may be in direct contact with the absorbent core.

The acquisition system 50 may comprise a single layer or multiple layers (not shown), such as an upper acquisition layer facing towards the wearer and a lower acquisition layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulose fibers and/or nonwoven webs.

Absorbent Core

The following describes an exemplary absorbent core of the invention.

For the invention, absorbent cores with high amounts of superabsorbent polymer material and low amounts of airfelt are analyzed in numerous respects and compared to absorbent cores having relatively high amounts of airfelt mixed with superabsorbent polymer material. It has been found that in currently available absorbent cores with high amounts of superabsorbent polymer material, fast liquid uptake in the superabsorbent polymer material is often inhibited to a certain extent as the superabsorbent polymer material is restricted from swelling upon first contact of the dry superabsorbent polymer material with liquid. Based on their findings, the inventors have found absorbent cores which allow for improved liquid uptake.

The laminate absorbent core 14 comprises a first, lower laminate layer 60 and a second, upper laminate layer 70. The first, lower laminate layer 60 comprises a first carrier substrate 62 and the second, upper laminate layer 70 comprises a second carrier substrate 72. The superabsorbent polymer material 80 is applied onto each of the first and second carrier substrates 62 and 72 such that the superabsorbent polymer material 80 forms multiple stripes 90 on each of the first and second carrier substrates 62 and 72. On each of the carrier substrates 62 and 72, the stripes of superabsorbent polymer material 90 are spaced apart from each other to form gaps 100 between neighboring stripes 90. The gaps 100 between neighboring stripes 90 are substantially free of superabsorbent polymer material 80. "Substantially free of superabsorbent polymer material" means that e.g. due to process-related reasons, a small, negligible amount of superabsorbent polymer material may be present in the gaps, which however does not contribute to the overall functionality. The term "substantially free of superabsorbent polymer material" encompasses the term "free of superabsorbent polymer material".

Before the first laminate layer 60 is joined to the second laminate layer 70 to form the laminate absorbent core 14, a first adhesive 110 is applied onto at least one of the first and second laminate layers 60 and 70. In one embodiment, the first adhesive 110 is applied onto the first and second laminate layer 60 and 70. The first adhesive 110 serves to at least partially immobilize the superabsorbent polymer material 80 both in dry and wet state. The first adhesive 110 is provided as a fibrous layer which is at least partially in contact with the superabsorbent polymer material 80 and partially in contact with the first and second carrier substrate 62 and 72. Typically, the first adhesive 110 forms a fibrous network.

To form the laminate absorbent core 14, the first and second laminate layer 60 and 70 are joined such that the first and second carrier substrates 62 and 72 face outwardly. The first and second laminate layers 60 and 70 are positioned on each other such that the superabsorbent polymer material stripes 90 of the second laminate layer 70 are overlaying the gaps 100 formed in the first laminate layer 60 and the superabsorbent polymer material stripes 90 of the first laminate layer 60 are overlaying the gaps 100 formed in the second laminate layer 70.

Each gap 100 in the first laminate layer 60 is wider than the corresponding superabsorbent polymer material stripe 90 of the second laminate layer 70 lying above the gap 100. Also, each gap 100 in the second laminate layer 70 is wider than the corresponding superabsorbent polymer material stripe 90 of the first laminate layer 60 lying below the gap 100. In the resulting laminate absorbent core 14, the superabsorbent polymer material 80 of the first laminate layer 60 does not contact the superabsorbent polymer material 80 of the second laminate layer 70 and vice versa. However, in embodiments wherein the gaps 100 between neighboring superabsorbent polymer material stripes 90 in either laminate layer have a small, negligible amount of superabsorbent polymer material due to process-related reasons and not contributing to the overall functionality, those small amounts in the gaps may be in contact with the superabsorbent polymer material stripes of the respective other layer.

Figure 2:
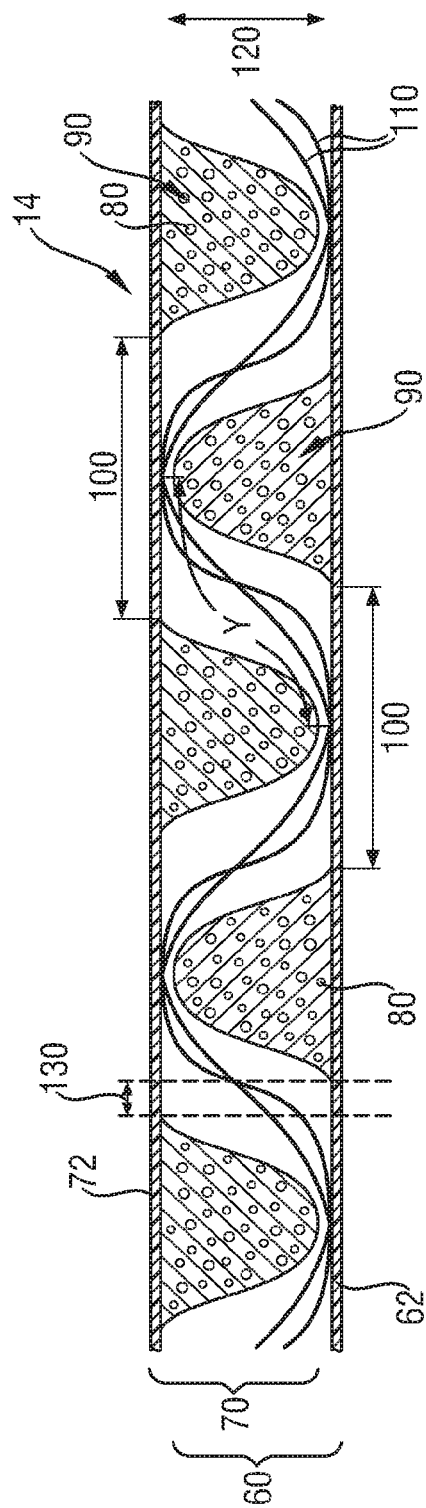
FIG. 2 is a schematic, partial cross sectional view of a laminate absorbent core in accordance with an embodiment of the invention
Figure 3:
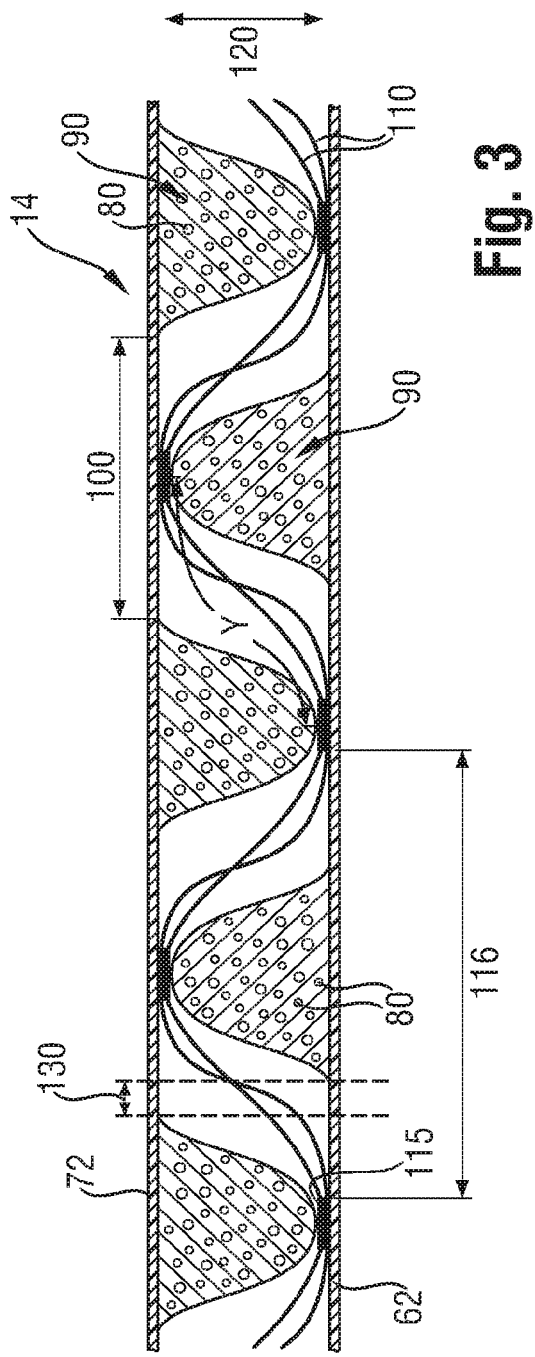
FIG. 3 is a schematic, partial cross sectional view of another laminate absorbent core in accordance with an embodiment of the invention

To ensure that, in the resulting laminate absorbent core 14, the superabsorbent polymer material 80 of the first laminate layer 60 does not contact the superabsorbent polymer material 80 of the second laminate layer 70 and vice versa, the superabsorbent polymer material stripes 90 of one laminate layer may be positioned adjacent to the gaps 100 of the respective other laminate layer such that the edge of the superabsorbent polymer material stripe 90 on the one laminate layer is spaced by at least 1 mm, or by at least 2 mm, or by at least 3 mm from the edge of the superabsorbent polymer material stripe 90 of the other laminate layer, which is positioned next to the respective superabsorbent polymer material stripe 90 in the laminate absorbent core 14 (indicated as 130 in FIGS. 2 and 3). This spacing 130 between neighboring superabsorbent polymer material stripes 90 of the laminate absorbent core 14 (where a superabsorbent polymer material stripe 90 of one laminate layer is neighboring a superabsorbent polymer material stripe 90 of the respective other laminate layer) may not be more than 10 mm or may not be more than 7 mm or may not be more than 5 mm. The spacing 130 between neighboring superabsorbent polymer material stripes 90 of the laminate absorbent core 14 may be such that the spacing 130 on both sides of a superabsorbent polymer material stripe 90 is the same or that the spacing 130 on one side is larger than the spacing of the other side.

In the laminate absorbent core 14, the first adhesive 110 forms a fibrous layer between the first and second laminate layer 60 and 70.

Once incorporated into an absorbent article 10 and in use of the article, the second, upper carrier substrate 72 is intended to be facing towards the wearer and the first, lower carrier substrate 62 is intended to be facing towards the garment. The second, upper carrier substrate 72 may be a nonwoven web or may, alternatively be a tissue. The first, lower carrier substrate 62 may be a nonwoven web, or may, alternatively be a tissue or a film. In an embodiment where the first, lower carrier substrate 62 is a film, the film may form at least part of the backsheet, or may be in addition to the backsheet. The second, upper and first, lower carrier substrate 62 and 72 may be made of the same material or they may be made of different material (i.e. the second carrier substrate 72 may be a nonwoven web while the first carrier substrate 62 may be a film). In embodiments wherein the second, upper and first, lower carrier substrate 62 and 72 are both nonwoven webs, these nonwoven webs may be the same nonwoven webs ore they may differ from each other, e.g. with regard to their basis weight, hydrophilicity, air permeability or number and/or type of layers comprised by the nonwoven webs. The type of layers may be spunbonded layers or meltblown layers. The nonwoven webs may also be carded webs made of staple fibers, and the carded webs may or may not comprise binder material. The nonwoven webs may also be hydro-entangled or needle-punched.

Optionally, no nonwoven webs, tissues or films are provided between the first and second laminate layer 60 and 70.

The first and second carrier substrate 62 and 72 may be attached to each other about their periphery to form an envelope about the superabsorbent polymer material 80 comprised by the laminate absorbent core 14. The first and second carrier substrate 62 and 72 may be attached to each other with adhesive or any other means known in the art such as ultrasonic bonding. In embodiments wherein the first and second carrier substrate 62 and 72 are nonwoven webs, the first and second carrier substrate may also be attached to each other by thermal and/or pressure bonding.

The first, lower carrier substrate 62 may be permeable or impermeable for liquids, such as urine. The second, upper carrier substrate 72 may be liquid permeable.

The laminate absorbent core 14 may comprise a second adhesive 115. If present, the second adhesive 115 is applied onto the first and/or second carrier substrate 62 and 72. There are different options for applying the second adhesive 115:

In one embodiment, the second adhesive 115 is applied onto the first and second carrier substrate 62 and 72 such that the second adhesive 115 extends in the areas below the superabsorbent polymer material stripes 90. In these embodiments, the second adhesive 115 has to be applied before the superabsorbent polymer material stripes 90 are formed on the first and second carrier substrates 62 and 72. The second adhesive may be applied on the whole surface of the first and/or second carrier substrate but optionally is only applied in certain regions. The second adhesive 115 can extend completely below the superabsorbent polymer material stripes 90. In any case, it is preferred that the second adhesive 15 is provided in the gaps 100 formed between the superabsorbent polymer materials stripes 90.

Optionally, the second adhesive 115 is applied such that the second adhesive forms stripes which are present at least in the gaps 100 between neighboring superabsorbent polymer materials stripes 90 on the first and/or second carrier substrates 62 and 72. The stripes of second adhesive 115 are separated from each other by gaps 116, which are substantially free of second adhesive. "Substantially free of second adhesive" means that e.g. due to process-related reasons, a small, negligible amount of second adhesive may be present in the gaps, which however does not contribute to the overall functionality. The term "substantially free of second adhesive" encompasses "free of second adhesive".

In embodiments wherein the second adhesive is applied in the form of stripes, the second adhesive stripes 115 may or may not extend below the neighboring superabsorbent polymer material stripes 90. If the second adhesive stripes 115 extend below the superabsorbent polymer material stripes 90, the second adhesive stripes 115 will be wider than the gaps 100 formed between neighboring superabsorbent polymer material stripes 90. The second adhesive stripes 115 may extend below the superabsorbent polymer stripes such that at least 5%, or at least 10%, or at least 20% or at least 50%, or at least 60%, of the area below the superabsorbent polymer material stripes is covered by second adhesive 115. Moreover, the second adhesive stripes 115 may extend below the superabsorbent polymer stripes such that less than 90%, or less than 75%, or less than 50%, or less than 25%, or less than 15%, or less than 10%, or less than 5% of the area below the superabsorbent polymer material stripes is covered by second adhesive 115.

If the second adhesive stripes 115 do not extend below the superabsorbent polymer material stripes 90 (as illustrated in FIG. 3), the second adhesive stripes 115 may have a narrower width than the gaps 100 formed between neighboring superabsorbent polymer material stripes 90 or they may have the same width than the gaps 100 formed between the superabsorbent polymer material stripes 90.

The second adhesive can either be applied to form a fibrous layer or the second adhesive can be applied to cover the respective area of the carrier substrate as a continuous, closed layer. Also when the second adhesive is applied in the form of stripes, these stripes may be formed as a continuous, closed layer of second adhesive or as a stripe of fine adhesive fibers, which form a continuous network, or in other configurations, such as rows of second adhesive spirals.

The second adhesive may be the same adhesive as the first adhesive or may be different than the first adhesive. Optionally, the second adhesive is a hot melt adhesive.

In the laminate absorbent core 14, the second adhesive 115 is at least partially in contact with the first adhesive 110 in the regions of the gaps 100 formed between the superabsorbent polymer material stripes 90. If the second adhesive 115 is applied on the first and second laminate layer 60 and 70, the first adhesive 100 is at least partially in contact with the second adhesive 115 on each of first and second laminate layers 60 and 70 (also if the first adhesive has been initially applied only to one of the first and second laminate layers).

Each laminate layer 60 and 70 of the laminate absorbent core 14 comprises multiple superabsorbent polymer material stripes 90. The number of superabsorbent polymer material stripes in each of the first and second laminate layer is at least 2. The number of superabsorbent polymer material stripes in each laminate layer may be at least 3 or 4 and may be less than 8 or may be less than 7 or less than 6. One of the laminate layers may have one superabsorbent polymer material stripe more than the respective other laminate layer.

The average basis weight of the superabsorbent polymer material in the superabsorbent polymer material stripes may be from 150 g/m$^2$ to 700 g/m$^2$, or from 200 g/m$^2$ to 600 g/m$^2$, or from 250 g/m$^2$ to 500 g/m$^2$. The basis weight of the superabsorbent polymer material may differ along the length of the superabsorbent polymer material stripe. Also, the basis weight of the superabsorbent polymer material may differ along the width of the superabsorbent polymer material stripe. This may especially be the case when the superabsorbent polymer material is applied in the shape of little humps, given the superabsorbent polymer material is flowable (especially when the superabsorbent polymer material is in the form of superabsorbent polymer particles). The average basis weight of the superabsorbent polymer material may also be different for different stripes comprised by the laminate absorbent core.

The basis weight of superabsorbent polymer material may or may not vary along the length of the laminate absorbent core. Often the core is profiled in its longitudinal direction. It has been found that, for most absorbent articles such as diapers, the liquid discharge occurs predominately in the front half of the diaper. The front half of the laminate absorbent core should therefore comprise most of the absorbent capacity of the core. Thus, according to certain embodiments, the front half of the laminate absorbent core 14 may comprise more than about 60% of the superabsorbent polymer material, or more than about 65%, 70%, 75%, 80%, 85%, or 90% of the superabsorbent polymer material based on the total superabsorbent polymer material provided in the laminate absorbent core. The average basis weight of the superabsorbent polymer material comprised by the laminate absorbent core may be from 100 g/m$^2$ to 500 g/m$^2$, or from 150 g/m$^2$ to 400 g/m$^2$ based on the surface area of the laminate absorbent core (i.e. the areas of the stripes of superabsorbent polymer material and of the gaps between these stripes). The surface area of the laminate absorbent core is defined by the x- and y-dimension of the laminate absorbent core. Any potential unevenness of the surface and irregularities of thickness (i.e. in the z-direction) is not taken into account. The x-,y-dimension of the laminate absorbent core is determined while the laminate absorbent core is lying flat on a table with not stress or strain applied (this also applies for potentially extensible absorbent cores). If needed, elastically contracting elements that otherwise would apply strain to the laminate absorbent core can be carefully removed prior to lying the laminate absorbent core flat on a table.

The superabsorbent polymer material stripes may be straight or they may take any other shape, such as curved, wavy or spiraled, though straight or curved superabsorbent polymer material stripes are preferred. The shape of the superabsorbent polymer material stripe may also be different for different stripes.

The width of one or more of the superabsorbent polymer material stripes in the laminate absorbent core may also vary along its length. Also, alternatively or in addition to a varying width of an individual superabsorbent polymer material stripe, different superabsorbent polymer material stripes of the laminate absorbent core may also have different width.

The width of each of the superabsorbent polymer material stripes may be at least 5 mm, or at least 10 mm, or at least 15 mm, or at least 20 mm, or at least 25 mm. The maximum width of the superabsorbent polymer material stripes will depend on the dimensions of the laminate absorbent core and the number of superabsorbent polymer materials stripes. The width of the superabsorbent polymer stripes may be less than 50 mm, or less than 40 mm or less than 30 mm. The gaps between the superabsorbent polymer material stripes within one laminate layer may have a width of greater than 6 mm, or greater than 11 mm, or greater than 16 mm, or greater than 21 mm, or greater than 26 mm. The gaps between the superabsorbent polymer material stripes within one laminate layer may have a width of not more than 52 mm, or not more than 42 mm, or not more than 32 mm.

The gaps 100 between the superabsorbent polymer material stripes 90 on each laminate layer is wider than the width of the superabsorbent polymer material stripe 90 of the respective other laminate layer, which is laying on top or below the respective gap. The width of the gap 100 may be at least 2 mm wider than the width of the respective superabsorbent polymer material stripe 90 which is lying beneath or above the respective gap 100. The width of the gap 100 between neighboring superabsorbent polymer material stripes 90 may be at least 3 mm wider or at least 4 mm wider than the width of the respective superabsorbent polymer material stripe 90 which is lying beneath or above the respective gap 100. The width of the gap 100 between neighboring superabsorbent polymer material stripes 90 may be not more than 15 mm, or not more than 10 mm, or not more than 8 mm wider than the width of the respective superabsorbent polymer material stripe 90 which is lying beneath or above the respective gap 100.

When the second adhesive, if present, is applied in stripes 115 within the gaps 100 between neighboring superabsorbent polymer materials stripes 90, the second adhesive stripes 115 may have a width of at least 1 mm or at least 2 mm or at least 3 mm or at least 4 mm. The width of the second adhesive stripe 115 may be less than 20 mm or less than 10 mm or less than 5 mm or less than 3 mm.

The laminate absorbent core 14 has a longitudinal direction (the length of the laminate absorbent core) with a longitudinal axis and a lateral direction (the width of the absorbent core) with a lateral axis. The longitudinal direction will generally be wider than the lateral direction. Also, the longitudinal direction is perpendicular to the lateral direction. When put in an absorbent article, the longitudinal axis of the laminate absorbent core is substantially parallel to the longitudinal axis of the absorbent article and the lateral axis of the laminate absorbent core is substantially parallel to the lateral axis of the absorbent article. "Substantially parallel" means that slight deviations, e.g. of up to 10° may occur. In one embodiment, the longitudinal axis of the laminate absorbent core is parallel to the longitudinal axis of the absorbent article and the lateral axis of the laminate absorbent core is parallel to the lateral axis of the absorbent article.

The laminate absorbent core further has a front region, a back region and a crotch region therein between and a front lateral edge, an opposing back lateral edge, and longitudinally extending side edges.

The front zone of the laminate absorbent core represents one third of the laminate absorbent core extending from the front edge of the laminate absorbent core along the longitudinal axis towards the crotch region. Once placed in an absorbent article, the front zone of the laminate absorbent core is placed towards the front waist edge of the absorbent article. The back zone represents one third of the laminate absorbent core extending from the back edge along the longitudinal axis towards the crotch region. Once put in an absorbent article, the back zone of the laminate absorbent core is placed towards the back waist edge of the absorbent article. The crotch zone represents the remaining third of the laminate absorbent core and extends between the front zone and the back zone. The complete length of the laminate absorbent core is defined as longest extension of the laminate absorbent core along or parallel to the longitudinal axis of the laminate absorbent core. The absorbent core of the invention may be rectangular. However, the laminate absorbent core may also take any other shape. In one embodiment, the crotch region of the laminate absorbent core has a narrower width than the front and back regions of the absorbent core. The shape of the laminate absorbent core of the invention is optionally axially symmetric with regard to the longitudinal axis of the laminate absorbent core. The shape of the laminate absorbent core of the invention may also be axially symmetric with regard to the lateral axis of the laminate absorbent core.

The laminate absorbent core of the invention may have a caliper of at least 1 mm, or at least 2 mm, or at least 3 mm. The caliper may be less than 20 mm, or less than 15 mm, or less than 10 mm, or less than 8 mm, or less than 5 mm. The caliper of the laminate absorbent core is measured at the point where the longitudinally axis crosses the lateral axis of the laminate absorbent core with no forces being applied on the laminate absorbent core (i.e. the laminate absorbent is neither compressed nor torn apart).

The superabsorbent polymer material stripes may extend in the longitudinal direction of the laminate absorbent core. Though less preferred, the superabsorbent polymer material stripes may alternatively extend in the lateral direction of the laminate absorbent core.

It is preferred that the superabsorbent polymer material stripes extend along the complete laminate absorbent core (for both options, longitudinally and laterally extending superabsorbent polymer material stripes). However the superabsorbent material stripes may also extend along only a part of the laminate absorbent core, such as not more than 90%, or not more than 75%, or not more than 50%, or not more than 25% of the longitudinal direction of the laminate absorbent core. The superabsorbent material stripes may extend along at least 50%, or at least 75% or at least 90% of the longitudinal direction of the laminate absorbent core. The superabsorbent polymer material stripes may also extend along not more than 90%, or not more than 75%, or not more than 50%, or not more than 25% of the lateral direction of the laminate absorbent core. The superabsorbent material stripes may extend along at least 50%, or at least 75% or at least 90% of the lateral direction of the laminate absorbent core.

For embodiments, wherein the superabsorbent polymer material stripes do extend only along a part of the longitudinal or lateral direction of the laminate absorbent core, the stripes may not extend to any of the lateral or longitudinal side edges of the absorbent core. The first, lower carrier substrate 62 of the laminate absorbent core 14 is facing towards the garment when the laminate absorbent core 14 is put in an absorbent article 10, such as a diaper or diaper-pant. The second, upper carrier substrate 72 is facing towards the wearer once the laminate absorbent core 14 is put in an absorbent article 10. Generally, the laminate absorbent core 10 is placed between the topsheet 18 and the backsheet 20 of the absorbent article 10. In absorbent articles which comprise a fluid acquisition system 50, the laminate absorbent core 14 is typically placed below the fluid acquisition system 50. However, it may alternatively be desirable to place the fluid acquisition system below the laminate absorbent core in an absorbent article.

The laminate absorbent core comprises absorbent material such as superabsorbent polymer material or airfelt (comprising cellulose fibers). The absorbent materials are contained within an upper and a lower carrier substrate.

The laminate absorbent core may be substantially free of absorbent material other than superabsorbent polymer material. For example, the absorbent material may comprise more than 80% by weight, optionally more than 90% by weight, more optionally more than 95% by weight and even more optionally more than 98% by weight of superabsorbent polymer material. In one embodiment all of the absorbent material comprised by the absorbent core is superabsorbent polymer material. If the laminate absorbent core comprises cellulose fiber (also sometimes referred to as "wood pulp", "fluff pulp" or "airfelt") in addition to the superabsorbent polymer material, the laminate absorbent core may comprise less than 5% by weight of cellulose fibers. Also, the cellulose fibers are optionally not provided in the gaps between neighboring superabsorbent polymer material stripes.

Superabsorbent Polymer Material

The superabsorbent polymer material will typically be in the form of superabsorbent polymer particles. The superabsorbent polymer particles may be of numerous shapes. The term "particles" refers to granules, fibers, flakes, spheres, powders, platelets and other shapes and forms known to persons skilled in the art of superabsorbent polymer particles. E.g. the particles can be in the form of granules or beads, having a particle size from about 10 μm to about 1000 μm, optionally from about 100 μm to about 1000 μm, even more optionally from about 150 μm to about 850 μm and most optionally from about 150 μm to about 500 μm. In another embodiment, the superabsorbent polymer particles can be in the shape of fibers, i.e. elongated, acicular superabsorbent polymer particles. In those embodiments, the superabsorbent polymer fibers have a minor dimension (i.e. diameter of the fiber) of less than about 1 mm, usually less than about 500 μm, and optionally less than 250 μm down to 50 μm. The length of the fibers is optionally about 3 mm to about 100 mm. The fibers can also be in the form of a long filament that can be woven.

Preferred superabsorbent polymer particles of the invention are spherical-like particles. According to the invention and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle.

The superabsorbent polymer materials useful in the invention include a variety of water-insoluble, but water-swellable polymers capable of absorbing large quantities of fluids. Such polymers materials are generally known in the art and include all those well-known polymers used or deemed useful in the context of disposable absorbent article technology.

Preferred polymer materials for use in making superabsorbent polymer materials are slightly network cross linked polymers of partially neutralized polyacrylic acids and starch derivatives thereof. Starch-based superabsorbent polymer materials are also encompassed in the invention. Optionally, the superabsorbent polymer materials comprise from 25% to 95% by weight, more optionally from 50% to 80% by weight neutralized, slightly network cross-linked, polyacrylic acid. Network cross-linking renders the polymer substantially water-insoluble and, in part, determines the absorptive capacity and extractable polymer content characteristics of the superabsorbent polymer material.

While the superabsorbent polymer materials is optionally of one type (i.e., homogeneous), mixtures of polymers can also be used in the invention. The superabsorbent polymer materials can also comprise mixtures with low levels of one or more additives, such as for example powdered silica, surfactants, adhesive, binders, and the like. Furthermore, the superabsorbent polymer particles can comprise a gradient in particle size or can comprise a certain range of particle size.

Many of the formerly known superabsorbent polymer particles exhibited gel blocking. "Gel blocking" occurs when particles made of the superabsorbent polymer materials are wetted and the particles swell so as to inhibit fluid transmission to other zones or regions of the absorbent structure. Wetting of these other regions of the absorbent core therefore takes place via a very slow diffusion process. In practical terms, this means acquisition of fluids by the absorbent structure is much slower than the rate at which fluids are discharged, especially in gush situations. Leakage from the absorbent article can take place well before the particles of superabsorbent polymer materials in the absorbent core are even close to being fully saturated or before the fluid can diffuse or wick past the "blocking" particles into the rest of the absorbent core.

One commonly applied way to reduce gel blocking is to make the particles stiffer, which enables the superabsorbent polymer particles to retain their original shape thus creating or maintaining void spaces between the particles. A well-known method to increase stiffness is to covalently and/or ionically cross-link the carboxyl groups exposed on the surface of the superabsorbent polymer particles. This method is commonly referred to as surface cross-linking.

First and Second Adhesive

The first and optional second adhesive comprised by the laminate absorbent core is optionally a hot melt adhesive. In certain, non-preferred embodiments, the first adhesive is a hot melt adhesive whereas the second adhesive may be another type of adhesive. The average basis weight of first plus optional second adhesive in the laminate absorbent core may be from 2 g/m$^2$ to 20 g/m$^2$, or from 2 g/m$^2$ to 1.0 g/m$^2$ based on the surface area of the laminate absorbent core. The average basis weight of the first adhesive alone in the laminate absorbent core may be from 1 g/m$^2$ to 18 g/m$^2$, or from 2 g/m$^2$ to 15 g/m$^2$ based on the surface area of the laminate absorbent core.

The first adhesive serves to at least partially immobilize the superabsorbent polymer material of the laminate absorbent core, both in dry and wet condition.

Without wishing to be bound by theory, it has been found that those hot melt adhesives which are most useful for immobilizing the superabsorbent polymer material combine good cohesion and good adhesion behavior. Good adhesion may promote good contact between the hot melt adhesive and the superabsorbent polymer material and the carrier substrates.

Good cohesion reduces the likelihood that the adhesive breaks, in particular in response to external forces, and namely in response to strain. When the laminate absorbent core absorbs liquid, the superabsorbent polymer material swells and subjects the hot melt adhesive to external forces. The hot melt adhesive may allow for such swelling, without breaking and without imparting too many compressive forces, which would restrain the absorbent particulate polymer material from swelling.

In accordance with an embodiment of the invention the hot melt adhesive may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the hot, melt adhesive may comprise at least one thermoplastic polymer in combination with other thermoplastic diluents such as tackifying resins, plasticizers and additives such as antioxidants.

In certain embodiments, the thermoplastic polymer typically has a weight average molecular weight (Mw) of more than 10,000 and a glass transition temperature ($T_g$) usually below room temperature (25° C.), or of less than 22° C., or less than 18° C., or less than 15° C. In certain embodiments $T_g$ may be above 0° C.>$T_g$. In embodiments where the thermoplastic polymer has more than one $T_g$ the values given refer to the lowest glass transition temperature. The thermoplastic polymer may also have a softening point, as determined by the ASTM Method D-36-95 "Ring and Ball", in the range between 50° C. and 300° C. In some embodiments the Mw of the thermoplastic polymer is less than 10000000.

In certain embodiments, typical concentrations of the thermoplastic polymer in a hot melt adhesive are in the range of about 20% to about 40% by weight of the hot melt adhesive.

Exemplary polymers are (styrenic) block copolymers including A-B-A-triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of $C_2$ to $C_8$ alpha olefins.

In exemplary embodiments, the tackifying resin has typically a Mw below 5,000 and a $T_g$ usually above room temperature (25° C.), typical concentrations of the tackifying resin in a hot melt are in the range of about 30% to about 60% by weight of the hot melt adhesive. In certain embodiments the tackifying resin has an Mw of more than 1,000.

The plasticizer has a low Mw of typically less than 1,000 and a $T_g$ below room temperature, with a typical concentration of about 0% to about 15% by weight of the hot melt adhesive. In certain embodiments the plasticizer has an Mw of more than 100.

In certain embodiments, the first and/or second adhesive is hot melt adhesive present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Method of Making the Laminate Absorbent Core

One method of making a laminate absorbent core comprises the following steps:

A first and a second carrier substrate are provided. Onto each of the first and second carrier substrate, multiple stripes of superabsorbent polymer material are formed. The stripes are formed such that neighboring stripes are separated by gaps.

After the stripes of superabsorbent polymer material are formed, a first adhesive is applied in the form of a fibrous layer on at least one of the first and second carrier substrates. In one embodiment, the first adhesive is applied on the first and second carrier substrate.

The first carrier substrate with the superabsorbent polymer material stripes formed thereon and the optional first adhesive applied on these stripes constitutes a first laminate layer and the second carrier substrate with the superabsorbent polymer material stripes formed thereon and the optional first adhesive applied on these stripes constitutes a second laminate layer.

Thereafter, the first and second laminate layers are combined to form a laminate absorbent core. The first and second carrier substrates are combined such the superabsorbent polymer material stripes face inwardly. The superabsorbent polymer material stripes on one carrier substrate are overlaying the gaps of the other carrier substrate and each gap on the first carrier substrate is wider than the corresponding superabsorbent polymer material stripe on the second carrier substrate, and also each gap on the second carrier substrate is wider than the corresponding superabsorbent polymer material stripe on the first carrier substrate.

In embodiments, wherein the first adhesive is only applied onto one of the first or second carrier substrates, it is preferred that the laminate layer having no first adhesive applied thereon is lying horizontally flat while the respective other laminate layer having the first adhesive applied is placed on top of the carrier substrate without first adhesive. The superabsorbent polymer material stripes of the carrier substrate having no first adhesive provided thereon may be held in place by vacuum, which is applied below the carrier substrate.

An alternative method of making a laminate absorbent core comprises the steps of
  providing a first carrier substrate;
  forming a first set of multiple stripes of superabsorbent polymer material on the first carrier substrate such that the stripes are spaced apart from each other to form gaps between neighboring stripes;
  applying a first adhesive in the form of a fibrous layer on the first carrier substrate on the surface comprising the superabsorbent polymer material stripes;
  forming a second set of multiple stripes of superabsorbent polymer material on the fibrous layer of the first adhesive, the second set of multiple stripes of superabsorbent polymer material being spaced apart from each other to form gaps between neighboring stripes;
  applying a second carrier substrate on top of the second set of superabsorbent polymer material stripes.

The first and second set of multiple stripes of superabsorbent polymer material are arranged such that the superabsorbent polymer material stripes of one set are overlaying the gaps of the superabsorbent polymer material stripes of respective other set. Each gap in the first set of superabsorbent polymer material stripes is wider than the corresponding superabsorbent polymer material stripe of the second set of superabsorbent polymer material stripes, and each gap in the second set of superabsorbent polymer material stripes is wider than the corresponding superabsorbent polymer material stripe of the first set of superabsorbent polymer material stripes.

In this alternative method, the first carrier substrate, the first set of multiple stripes of superabsorbent polymer material and the first adhesive together are considered to form a first laminate layer. The second carrier substrate together with the second set of multiple stripes of superabsorbent polymer material forms a second laminate layer.

For both methods, the following applies:

The number of superabsorbent polymer material stripes in each of the laminate layers may be from 3 to 8, or from 4 to 6.

The width of each of the superabsorbent polymer material stripes may be at least 5 mm, or at least 10 mm, or at least 15 mm, or at least 20 mm, or at least 25 mm. The maximum width of the superabsorbent polymer material stripes will depend on the dimensions of the laminate absorbent core and the number of superabsorbent polymer materials stripes. The width of the superabsorbent polymer material stripes may be less than 50 mm, or less than 40 mm or less than 30 mm. The gaps between the superabsorbent polymer material stripes within one laminate layer may have a width of greater than 6 mm, or greater than 1.1 mm, or greater than 16 mm, or greater than 21 mm, or greater than 26 mm. The gaps between the superabsorbent polymer material stripes within one laminate layer may have a width of not more than 52 mm, or not more than 42 mm, or not more than 32 mm.

The width of the gap in one laminate layer may be at least 2 mm wider than the width of the superabsorbent polymer material stripe of the other laminate layer, which is lying on top or below the respective gap. The width of the gap between neighboring superabsorbent polymer material stripes may be at least 3 mm wider or at least 4 mm wider than the width of the respective superabsorbent polymer material stripe which is lying beneath or above the respective gap. The width of the gap between neighboring superabsorbent polymer material stripes may be not more than 15 mm, or not more than 10 mm, or not be more than 8 mm wider than the width of the respective superabsorbent polymer material stripe which is lying beneath or above the respective gap.

To ensure that in the resulting laminate absorbent core the superabsorbent polymer material of the first laminate layer does not contact the superabsorbent polymer material of the second laminate layer and vice versa, the superabsorbent polymer material stripes of one laminate layer may be positioned adjacent to the gaps of the respective other laminate layer such that the edge of the superabsorbent polymer material stripe on the one laminate layer is spaced by at least 1 mm, or by at least 2 mm, or by at least 3 mm from the edge of the superabsorbent polymer material stripe of the other laminate layer, which is positioned next to the respective superabsorbent polymer material stripe in the laminate absorbent core. This spacing between neighboring superabsorbent polymer material stripes of the final laminate absorbent core (where a superabsorbent polymer material stripe of one layer is neighboring a superabsorbent polymer material stripe of the respective other layer) may not be more than 10 mm or may not be more than 7 mm or may not be more than 5 mm, or may not be more than 3 mm. The spacing between neighboring superabsorbent polymer material stripes of the laminate absorbent core may be such that the spacing on both sides of a superabsorbent polymer material stripe is the same or that the spacing on one side is larger than the spacing of the other side.

Both methods may also comprise a step of applying a second adhesive onto the first and/or second carrier substrate such that the second adhesive is applied at least in the gaps between the superabsorbent polymer material stripes. The second adhesive may also be applied below the superabsorbent polymer material stripes of the respective laminate layer. The optional second adhesive should be applied such that, in the laminate absorbent core, the first adhesive is in contact with the second adhesive of the first and/or second carrier substrate in the regions of the gaps between the superabsorbent polymer material stripes.

The optional second adhesive may be applied in the form of multiple stripes on at least one of the first and second carrier substrates such that, in the laminate absorbent core, the first adhesive is in contact with the second adhesive, and wherein the second adhesive stripes extend below the neighboring superabsorbent polymer material stripes of the respective laminate layer by at least 1% and by less than 50% of width of the neighboring superabsorbent polymer material stripe. Alternatively, the second adhesive stripes do not extend below neighboring superabsorbent polymer material stripes but the second adhesive stripes are only applied in the gaps between the superabsorbent polymer material stripes. The second adhesive stripes may have a width of at least 1 mm or at least 2 mm or at least 3 mm or at least 4 mm. The width of the second adhesive stripes may be less than 20 mm or less than 10 mm or less than 5 mm or less than 3 mm.

The second carrier substrate may be a nonwoven web or may, alternatively, be a tissue. The first, carrier substrate may be a nonwoven web, or may, alternatively be a tissue or a film. If the first carrier substrate is a film, this carrier substrate should be facing towards the garment facing surface of an absorbent article while the second carrier substrate should be facing towards the wearer-facing surface of the absorbent article, once the laminate absorbent core is incorporated into an absorbent article.

In both methods of making the laminate absorbent core, less than 5% by weight of cellulose fibers based on the total weight of the laminate absorbent core may be comprised in the resulting laminate absorbent core.

In both methods of making the laminate absorbent core, the first and second carrier substrates may be provided on a supporting substrate, such as a conveyor belt. Below the supporting substrate, a vacuum may be applied to ensure that the carrier substrates are sufficiently immobilized on the supporting substrates.

The supporting substrate may also be in the form of a drum. In such embodiments, the first and second carrier substrates may be held in place on the surface of the supporting drum by and underlying vacuum.

In the method wherein the first laminate layer and the second laminate layer are formed independently from each other and are joined to each other after being formed, the first carrier substrate may be provided on a first drum and the second carrier substrate may be provided on a second drum until the moment, in which the first and second laminate layers are combined with each other. Upon combining the first laminate layer with the second laminate layer, the resulting laminate absorbent core may be provided on either the first or second drum or may, alternatively, be provided on a third drum or other supporting substrate, such as a conveyor belt. The resulting laminate absorbent core may also be directly placed on other components of an absorbent article, such as the backsheet, acquisition system or topsheet, or on a combination of the topsheet and the acquisition system.

All other optional features and components set out above with regard to the laminate absorbent core and its first and second laminate layers are equally applicable to the methods of manufacturing the laminate absorbent core.

Laminate Compression Extension

To simulate closely the forces which occur when the superabsorbent polymer material within the laminate absorbent core swells and expands upon absorption of liquid, leading to a general expansion of the laminate absorbent core, the laminate absorbent core is subjected to the Laminate Compression Extension Test as described in detail below.

In this test, a dry laminate absorbent core is pulled apart in the z-direction of the absorbent core and the force is measured, which is required to pull the laminate absorbent core apart and the pressure, which the laminate absorbent core exerts upon being pulled apart.

As Comparative Example 1 (see below), the absorbent core of Pampers "Active Fit", Size 4 as commercially available in Germany in May 2011, which is a disposable diaper having a laminate absorbent core with no airfelt (cellulose fibers) has been subjected to the Laminate Compression Extension Test.

In the laminate absorbent core of Pampers "Active Fit", the superabsorbent polymer material is provided in two layers within an upper and a lower nonwoven carrier substrate. The superabsorbent polymer material is immobilized between the upper and lower nonwoven web by a hot melt adhesive in the form of a fibrous layer, which is applied between the superabsorbent polymer material of the upper laminate layer and the superabsorbent polymer material of the lower laminate layer.

It has been found that the force required to pull such a laminate absorbent core apart steeply increases for the initial phase of pulling. After the laminate absorbent core has been pulled apart slightly (about 1 to 3 mm), the force required to pull the laminate absorbent core further apart quickly decreases to an extent that only relatively small forces are needed to pull the laminate absorbent core further apart.

Considering a situation, wherein such a laminate absorbent core is placed in an absorbent article, such as a disposable diaper, this finding suggests, that upon the initial absorption of liquid, fast expansion of the superabsorbent polymer material comprised in the laminate absorbent core is hindered to a certain extent. This may result in delayed absorption of liquid, increasing the risk of diaper leakage.

Without wishing to be bound by theory, the inventors of the invention believe, that the relatively high amount of forces which need to be applied upon initial expansion of the laminate absorbent core in the z-direction (i.e. in the thickness direction of the absorbent core), might be due to the structure of the fibrous network of adhesive material applied between the upper and lower laminate layers.

Figure 4:
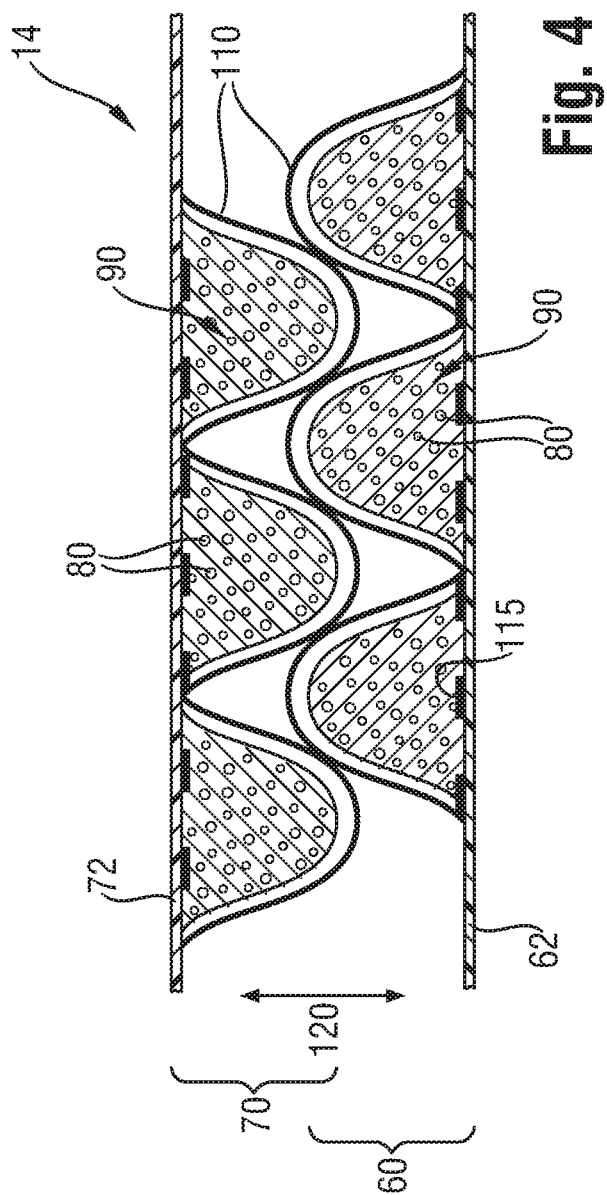
FIG. 4 is a schematic, partial cross sectional view of a laminate absorbent core of the prior art

In the currently available laminate absorbent cores having little or no airfelt between the upper and lower carrier substrates, the superabsorbent polymer material is applied such that a generally continuous layer of superabsorbent polymer material is provided. This can be achieved for example by applying superabsorbent polymer material in a discontinuous manner in the individual upper and lower laminate layer (such as in the form of "islands" of superabsorbent polymer material which are at least partly surrounded by areas with no superabsorbent polymer material) and combining the upper and lower laminate layer in a way that the superabsorbent polymer material is provided generally continuous between the upper and lower carrier substrates. In such embodiments, the "islands" of superabsorbent polymer materials in the respective layers overlap each other to a certain extent upon combining the upper and lower layer together. Such an embodiment of the prior art is shown in FIG. 4.

At least part of the adhesive (the first adhesive) is applied as an adhesive fibrous network between the upper and lower laminate layers, that is, an adhesive fibrous layer is provided on top of the superabsorbent polymer material of each layer immediately prior to combining the upper and lower laminate layer. Upon joining the upper and lower laminate layer together, it is believed that in the course of this combination, at least a part of the adhesive fibers comprised in one laminate layer stick to at least a part of the adhesive fibers of the respective other laminate layer (shown in FIG. 4). In such laminate absorbent cores of the prior art few adhesive fibers of an adhesive fibrous network initially applied on one laminate layer are believed to extend all the way through the thickness of the absorbent laminate core from one carrier substrate to the other, being adhered to both, the upper and lower carrier substrate. Instead, an adhesive fiber of the adhesive fibrous network of one laminate layer may be attached to the carrier substrate of this laminate layer and may extend from the carrier substrate through a part of the thickness of the absorbent core where it is stuck to an adhesive fiber of the adhesive fibrous network of the other laminate layer. Vice versa, an adhesive fiber of the adhesive fibrous network of the respective other laminate layer may be attached to the carrier substrate of this other laminate layer and may extend from the this carrier substrate through a part of the thickness of the absorbent core where it is stuck to an adhesive fiber of the adhesive fibrous network of the other laminate layer. Hence, relatively many adhesive fibers of the fibrous network of one laminate layer may adhere to adhesive fibers of the fibrous network of the respective other laminate layer.

Also, few adhesive fibers may extend from the upper carrier substrate between the particles of the superabsorbent polymer materials onto the lower carrier substrate (i.e. these fibers are adhered to the upper and lower carrier substrate). However, as the superabsorbent polymer material is applied substantially continuously in the laminate absorbent core between the upper and lower carrier substrate, the adhesive fibers extending from the upper carrier substrate onto the lower carrier substrate and being adhered to the upper and lower carrier substrate are "squeezed" between the superabsorbent polymer material and will thus span a relatively short distance, i.e. they will take a short path defined by a relatively straight line between the upper and lower laminate layer. Hence, upon expansion of the laminate absorbent core in the z-direction, these adhesive fibers have to elongate to be able to follow expansion without breaking. Since the adhesive fibers typically have certain elastic properties, elongation of the adhesive fibers is generally possible. However, elongation of adhesive fibers requires a certain amount of force. This theory is supported by the finding that when a sample derived from a Pampers Active fit diaper (Comparative Example 1) is subjected to the Laminate Compression Extension Test, the initial force needed to separate the laminate absorbent core in the z-direction is relatively high (see graph in FIG. 7).

Furthermore, while the adhesive fibrous network is initially applied onto the superabsorbent polymer material of a laminate layer at high temperature and thus in a state of relatively low viscosity, the temperature of the adhesive fibrous network will have decreased to a certain extent when the upper and lower laminate layer are joined to each other. Even if the step of joining the laminate layers to each other takes place immediately after step of applying the adhesive fibrous network, the adhesive fibrous network will have cooled down to a certain extent compared to the temperature, at which the adhesive was applied on the laminate layer, especially given the adhesive fibers have high surface area compared to their volume, which promotes fast temperature drop. As the temperature of the adhesive fibrous network is lowered, the viscosity of the fibrous network increases. As a consequence, the adhesive fibers of the upper laminate layer, when coming into contact with the adhesive fibers of the lower laminate layer, will not be able to form a joint that is as stable as the integral adhesive fibrous network applied on the respective laminate layers. Consequently, the contact areas between the first, lower and second, upper fibrous network are more prone to separation upon pulling the laminate absorbent core apart in the z-direction compared to separation of the adhesive fibers within an adhesive fibrous network of a given laminate layer. Such tendency to separate might lead to delamination of the laminate absorbent core.

Hence, upon expansion of the laminate absorbent core in the z-direction, the adhesive fibrous network is most likely prone to delaminate at the locations, where the adhesive fibers of one layer got stuck and adhered to the adhesive fibers of the other layer. This tendency to adhesive fiber delamination is supported by the finding that, after the initial phase of laminate separation in the z-direction has required relatively high forces, there is a relatively pronounced drop in the required force after the laminate layers have been separated by some millimeters (see graph in FIG. 7): Once the fibrous network initially applied to the lower laminate layer has delaminated to a relatively large degree from the fibrous network initially applied to the upper laminate layer, the upper and lower laminate layer are relatively easy to separate, which is reflected by the considerably lower forces needed to separate the laminate further compared to the initial high forces.

It is neither desirable that the laminate absorbent core requires very high initial forces for laminate layer separation the z-direction, nor is it desirable to have a drastic drop in the forces needed for separation after an initial phase: The high forces required in the initial phase may result in delayed liquid absorption and thus, increased risk of leakage. A significant drop of forces below a certain level may result in reduced immobilization of the superabsorbent polymer materials comprised in the laminate absorbent core, as the fibrous network, which is meant to immobilize the superabsorbent polymer material, is weakened, leading to delamination and reduced integrity of the laminate absorbent core.

Based on these insights gained by the inventors, laminate absorbent cores are needed, which, when subjected to the Laminate Compression Extension Test described below, requires relatively low forces upon initial separation of the laminate absorbent core in the z-direction (peak swelling restriction pressure). Also, the forces needed to separate the laminate layers should not drop below a certain threshold upon further separation (which would be an indication for a relatively high degree of delamination) to ensure sufficient superabsorbent polymer material immobilization for laminate absorbent cores which are in the wet state (wherein a certain expansion and separation of the laminate layers in the z-direction has occurred).

One possible embodiment of a laminate absorbent core which fulfills these requirements is described in great detail above. However, other embodiments are also within the scope of the invention, such as embodiments, wherein the superabsorbent polymer material is applied in dots or other shapes or any laminate absorbent core configuration, wherein the following is facilitated:

The superabsorbent polymer material and the fibrous layer of first adhesive is configured such, that at least some of the adhesive fibers, which are adhered to and extending from one carrier substrate to the other in the z-direction of the laminate absorbent core, are enabled to take a longer path compared to the shortest, straight line between the upper and lower laminate layer. Moreover, it is desirable that a higher number of adhesive fibers is attached both to the first and to the second carrier substrate. These aspects can be facilitated especially by joining the first and second laminate layer such, that the superabsorbent polymer material is not distributed generally continuously between the upper and lower laminate layer but that interstices are formed where little or no superabsorbent polymer material is present. By doing so, at least some of the adhesive fibers can take a more inclined path between the first and second carrier substrate (indicated as Y in FIGS. 2 and 3), resulting in a longer adhesive fiber extending between the first and second carrier substrate compared to adhesive fibers taking a straight path.

By providing such longer distance between the locations wherein a given adhesive fiber is attached to the first and second carrier substrate, the fibers can "stand up" and straighten up upon expansion the laminate absorbent core in the z-direction. Compared to elongation of an adhesive fiber, which, as set out above, is required for adhesive fibers taking the direct, shortest path between the first and second laminate layers in the dry, unexpanded laminate absorbent core, such straightening up of adhesive fibers without the initial need for adhesive fiber elongation requires considerably less force.

These findings are reconfirmed by Example 1 given below (see graph in FIG. 6): For laminate absorbent cores which have a structure as the one explained in detail above in the section "Absorbent Core" considerably less forces are required for initial laminate layer separation (peak swelling restriction pressure) compared to currently available laminate absorbent cores wherein superabsorbent polymer particles are substantially continuously supplied between the first and second carrier substrate.

Also, a relatively high number of adhesive fibers appear to be attached to both, the first and second carrier substrate, such that the delamination tendency of the laminate absorbent core—when the core is further pulled apart—is reduced. This is reflected by the fact, that the force needed to separate the laminate layers at 20 mm is higher in Example 1 compared to the Comparative Example 1. This so-called "Pressure at 20 mm" is the pressure exerted by the laminate absorbent core when it has been pulled apart in the z-direction such that the thickness of the absorbent core (i.e. extension in z-direction 120 as shown in FIGS. 2 to 4) is 20 mm when subjected to the Laminate Compression Extension Test.

In embodiments having a second adhesive, as explained in detail above, the second adhesive may improve adhesion of the first adhesive to the carrier substrate. The second adhesive is typically applied directly onto the first and/or second carrier substrate such that the second adhesive is positioned below any superabsorbent polymer material. The first adhesive is thus—at least partly—attached to the carrier substrate indirectly via the second adhesive. However, a part of the first adhesive may still be directly attached to the carrier substrate.

While in the Laminate Compression Extension Test described herein the core is separated in z-direction in the dry state, the behavior of a wet laminate absorbent will not differ significantly from the behavior in the dry state. The adhesive fibers of the first adhesive adhere to each other, to the first and second carrier substrate and to the optional second adhesive, and they also adhere to the superabsorbent polymer material. However, as the superabsorbent polymer material gets wet and expands, the attachment of the adhesive fibers to the superabsorbent polymer material is weakened, as the adhesive strength between the adhesive fibers of the first adhesive and wet superabsorbent polymer material is lower compared to the adhesive strength between the adhesive fibers and dry superabsorbent polymer material. Hence, upon wetting and swelling of the superabsorbent polymer material, the adhesive fibers of the second adhesive will largely detach from the superabsorbent polymer material. Therefore, there is no significant difference between expansion in z-direction in dry and wet state of the laminate absorbent core: When expanding in the wet state, the adhesive fibers will detach from the swollen superabsorbent polymer material, and hence, the superabsorbent polymer material will not affect the behavior of the adhesive fibers. When expanding in the dry state, the adhesive fibers will partly detach from the superabsorbent polymer material and the remaining superabsorbent polymer material, which remains attached to the adhesive fibers, will move together with the adhesive fibers. However, the adhesive fibers still entangle the superabsorbent polymer material, thereby facilitating immobilization of the superabsorbent polymer material.

Comparative Example 1

Pampers "Active fit" diapers as commercially available in Germany in May 2011. Size 4

Comparative Example 2

Pampers "Baby Dry" diapers as commercially available in Germany in May 2011. Size 4. (Note: The absorbent core of diaper contains airfelt with superabsorbent polymer particles mixed with the airfelt)

Example 1

Example 1 is a laminate absorbent core with two laminate layers, a first, lower and a second, upper laminate layer.

Upper Laminate Layer

A 390 mm long and 165 mm wide nonwoven web (SMS, i.e. spunbond-meltblown-spunbond layers) made of polypropylene and having a basis weight of 10 g/m² was used as second upper carrier substrate. 5 stripes of the second adhesive (hot melt adhesive) were applied in the longitudinal direction, each stripe having a width of 2 mm and covering a whole length of the product what is 390 mm. The distance between the center (referring to the width of the stripe) of two adjacent, neighboring second adhesive stripes was 20 mm. The basis weight of the second adhesive in each stripe was 116 g/m². The second adhesive is the same material as the second adhesive in Comparative Example 1.

Next to each second adhesive stripe, a 8 mm wide and 360 mm long stripe of super absorbent polymer material is placed, such that the number of superabsorbent polymer material stripes is 6. The superabsorbent polymer adhesive stripes are applied leaving a gap of 15 mm to front and back edge of the carrier substrate. The distance between the center (referring to the width of the stripe) of two adjacent, neighboring superabsorbent polymer material stripes is 20 mm, resulting in a distance between the center of the superabsorbent polymer material stripe to the center of the neighboring second adhesive stripe of 10 mm. The superabsorbent polymer material is the same as the one applied in Comparative Example 1. The overall amount of superabsorbent polymer material in the lower laminate layer is 10 g, which are evenly distributed on the 6 superabsorbent polymer material stripes.

Subsequent to the application of the superabsorbent polymer material stripes, a net of first adhesive is evenly applied, having an average basis weight of about 10 g/m² and a width of 108 mm, covering the whole length of the product. The first adhesive is applied in the same way as in Comparative Example 1 and the first adhesive also consists of the same material as the first adhesive of Comparative Example 1.

Lower Laminate Layer

A 390 mm long and 130 mm wide nonwoven web (SMS, i.e. spunbond-meltblown-spunbond layers) made of polypropylene and having a basis weight of 11 g/m² was used as first, lower carrier substrate.

6 stripes of the second adhesive (hot melt adhesive) were applied in the longitudinal direction, each stripe having a width of 2 mm and covering a whole length of the product what is 390 mm. The distance between the center (referring to the width of the stripe) of two adjacent, neighboring second adhesive stripes was 20 mm. The basis weight of the second adhesive in each stripe was 97 g/m². The second adhesive is the same material as the second adhesive in Comparative Example 1.

Next to each second adhesive stripe, a 8 mm wide and 360 mm long stripe of superabsorbent polymer material is placed, such that the number of superabsorbent polymer material stripes is 5. The superabsorbent polymer adhesive stripes are applied leaving a gap of 15 mm to front and back edge of the carrier substrate. The distance between the center (referring to the width of the stripe) of two adjacent, neighboring superabsorbent polymer material stripes is 20 mm, resulting in a distance between the center of the superabsorbent polymer material stripe to the center of the neighboring second adhesive stripe of 10 mm. The superabsorbent polymer material is the same as the one applied in Comparative Example 1. The overall amount of superabsorbent polymer material in the lower laminate layer is 10 g, which are evenly distributed on the 5 superabsorbent polymer material stripes.

Subsequent to the application of the superabsorbent polymer material stripes, a net of first adhesive is evenly applied, having an average basis weight of about 10 g/m² and a width of 108 mm, covering the whole length of the product. The first adhesive is applied in the same way as in Comparative Example 1 and the first adhesive also consists of the same material as the first adhesive of Comparative Example 1.

Combination of Upper and Lower Laminate Layer

The upper and lower laminate layers are placed together such that the surfaces of both carrier substrates, which not covered by superabsorbent polymer material are facing outwardly. Thereby the laminate absorbent core is formed with the superabsorbent polymer material (and the first and second adhesive) encased between the first and second carrier substrate.

When the two layers are combined, the center (referring to the width) of each of the top superabsorbent polymer material stripes of the upper laminate layer bars overlays and contacts the center of the respective second adhesive stripe of the lower laminate layer and vice versa. Hence, each superabsorbent polymer material stripe of the upper layer is placed centrally in the respective gap between two superabsorbent polymer material stripes of the lower laminate layer and vice versa. The superabsorbent polymer material stripes of one laminate layer do not touch the superabsorbent polymer material stripes of the respective other laminate layer.

The longitudinal edges of the second, upper carrier substrate of the upper laminate layer is folded over along the longitudinal side edges of the first, lower carrier substrate of the lower laminate layer onto the surface of the first, lower carrier substrate which, when the laminate absorbent core is put into an absorbent article, is facing towards the garment of the wearer (when the article is in use). Upon folding, also the first, lower carrier substrate is slightly folded over outwardly, such that the final width of the laminate absorbent core is 120 mm. The folded areas of the both carrier substrates are adhesively attached and thus fixed in their folded configuration.

The Example and the Comparative Examples were subjected to the Laminate Compression Extension Test Method to measure the peak swelling restriction pressure and the swelling restriction pressure at 20 mm.

It has been found that it is desirable to have laminate absorbent cores exhibiting a peak swelling restriction pressure from 50 N/m² to 400 N/m², or from 100 N/m² to 300 N/m², or from 150 N/m² to 300 N/m². Also, the laminate absorbent cores may have a swelling restriction pressure at 20 mm of more than 30 N/m², or from 30 N/m² to 100 N/m², or from 40 N/m² to 100 N/m². The ratio of peak swelling restriction pressure to swelling restriction pressure at 20 mm may be from 1 to 10. or from 2 to 8, or from 2 to 6.

Laminate Compression Extension Test

The method determines the swelling restriction pressure that is applied on the superabsorbent polymer material by the first adhesive in the laminate absorbent core in dependency of separation of the laminate absorbent core in the z-direction.

Equipment

Analytical Balance with an accuracy of at least 0.01 g.
Vernier caliper with a length of at least 100 mm and a sensitivity resolution of ±0.05 mm
Chamber capable to be controlled up to a temperature of 37° C. (+/−1° C.)
Vertical Single column Zwick Tensile Tester machine inside the temperature chamber with Zwick Roell Load cell which has maximum compression force of 50 N with force accuracy of 0.3% and distance accuracy of 0.15% or equivalent instrument
Double sided adhesive tape from teas SE "tesa Bastelband beidseitig klebend" 56665-0001, 2.75 m×38 mm
Two T-shaped sample holders made out of Plexiglas
Elastic natural rubber foam with 3 mm thickness to cover surface of T-shaped sample holders: Supplier: KKT GmbH, Siegen, Germany. Material description: "Zellkautschukstreifen EPDM Schwarz, einseitig selbstklebend als Montagehilfe mit Klebertyp VI in 10 m Rollen 90×3 mm"
Alfa Hydraulic Sample Cutter. E.g. from, Thwing-Albert Instrument Company, Alfa hydraulic precision sample cutter, serial no: 4450, 19154 catalog 240-10 or equivalent, with 60 mm diameter circular cutter, e.g. Karl Reichert GmbH, Rheinstr. 5, 86955 Pirmasens
Marker (e.g. ball point pen, fine tip)
Metal Ruler traceable to NIST, DIN, JIS or other comparable national standard, graduated in mm.
Computer connected with Zwick Tensile Tester machine and installed with acquisition program 'testXpert' software version 10.0, software provider: Zwick GmbH & Co, D-89079 Ulm, or equivalent.

Test Setup

Figure 5:
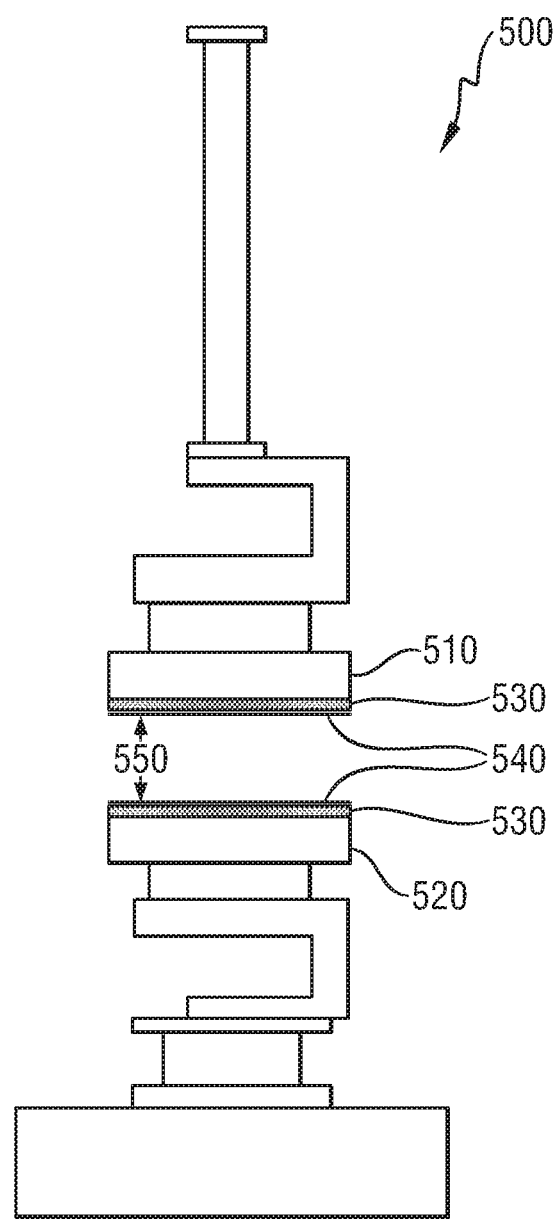
FIG. 5 is a schematic drawing of a Zwicker tensile tester used in the Laminate Compression Extension Test

FIG. 5 shows the setup of the Zwick Tensile Tester 500 as used for the Laminate Compression Extension Test.

The system consists of the following main parts:

Upper sample holder 510 made of Plexiglas, movable up and down
Lower sample holder 520 made of Plexiglas
Elastic natural rubber foam 530 used as damping adhesively attached to both sample holders, covered with double sided adhesive tape 540
Load Cell measuring compression and extension in the range of −50 N-50 N
The upper and lower sample holder need to be large enough to support and accommodate the complete sample.

Method

The test sample can be either prepared out of a complete absorbent article or, alternatively, can be prepared from a laminate absorbent core which has not been incorporated into an absorbent article before. (As illustrated by Comparative Example 2, the method can generally also be applied to absorbent cores which are not laminate absorbent cores but which comprise a mixture of superabsorbent polymer material with airfelt).

If the test sample is taken from the laminate absorbent core which has previously been incorporated into an laminate absorbent article, the following procedure needs to be followed to isolate the laminate absorbent core from the absorbent article:

All layers of the absorbent article above and below the laminate absorbent core are carefully removed. The laminate absorbent core of the invention has an upper and a lower carrier substrate (typically a nonwoven web, a tissue or a film) with the superabsorbent polymer material encased in between these carrier substrates. Hence, the laminate absorbent core can be clearly identified in absorbent articles encompassed by the invention.

If any layers are strongly attached to the laminate absorbent core such that they only be partly removed, those layers should be removed to the extent possible without damaging or destroying the laminate absorbent core. If a layer cannot be removed at all due to strong attachment to the laminate absorbent core, this layer will remain on the laminate absorbent core for the further test procedure. The strength of this attachment will be stronger compared to the forces measured in the method herein and therefore this/these layer(s) will have no significant influence on the data obtained.

On the longitudinal axis of the laminate absorbent core mark a first point at a distance of 145 mm from the front laminate absorbent core edge and a second mark at a distance of 205 mm from front laminate absorbent core edge. A 60 mm diameter circle is cut out between these two marks with the center of the circle being on the longitudinal axis of the laminate absorbent core. This circular cut out represents the test sample.

Both Plexiglas sample holders are covered with the elastic natural rubber foam. Double sided tape is attached on the natural rubber foam of both Plexiglas sample holders over the whole surface of the test sample holders.

The test sample is attached to the double sided tape of the lower sample holder with the lower carrier substrate of the test sample facing downwards (i.e. the lower carrier substrate is attached to the sample holder).

The lower sample holder is then put in the lower clamp of the Zwick Tensile Tester apparatus and the upper sample holder is put in the upper clamp of the Zwick Machine such that the upper and lower sample holder are fully congruent with each other.

The complete set up including the Zwick Tensile Tester apparatus with the test sample is heated to a temperature of 37° C. in the climate chamber at a relative humidity of 50%+/−5%. Once the temperature is reached, the temperature and relative humidity is maintained for 5 minutes before the further method steps are carried out. The temperature and relative humidity are also maintained throughout the following method steps.

The upper sample holder is moved down at a speed of 20 mm/min until a compression of 50 N is reached. Thereby, reliable attachment of the sample to the upper and lower sample holder is achieved.

Then the upper sample holder is moved up at a speed of 2.5 mm/min until a compression of 5.844 N is reached. The distance between the rubber foams on the upper and lower sample holder represents the caliper of the sample when compressed with a force of 5.844 N. (The initial caliper of the sample is the caliper without any force being applied on the sample. This initial caliper of the sample represents the caliper of the laminate absorbent core of the invention).

- Now the upper sample holder is moved up further at a speed of 0.085 mm/second until a sample caliper of 11.78 mm (=distance between upper and lower sample holder) is reached.
- Immediately thereafter, the upper sample holder is moved up at a speed of 0.023 mm/second until a sample caliper of 15.96 mm (=distance between upper and lower sample holder) is reached.
- Immediately thereafter, the upper sample holder is moved up at a speed of 0.009 mm/second until a sample caliper of 18.63 mm (=distance between upper and lower sample holder) is reached.
- Immediately thereafter, the upper sample holder is moved up at a speed of 0.003 mm/second until a sample caliper of 20.32 mm (=distance between upper and lower sample holder) is reached.

At the end of the test, upper sample holder is moved further upwards to remove the sample and sample holders. The test is then stopped. The tensile forces are measured continuously during the above steps indicated with bullet points.

The software for the acquisition program 'testXpert' inter alia provides the data on Standard Force [N] and LE channel 550 [mm]. The LE channel data is set to represent the distance between the rubber foams of the upper and lower sample holder and thus the caliper of the sample. To obtain the pressure in [N/m$^2$] the Standard Force values in [N] are divided by the area of the test sample, that is calculated to □*(0.03 m)2=0.0028 N/m$^2$.

The Peak Pressure is the highest pressure value within a caliper range up to 20 mm. For the pressure at 20 mm caliper the pressure value is taken for the caliper first reaching 20 mm. Both values are reported.

Figure 6:
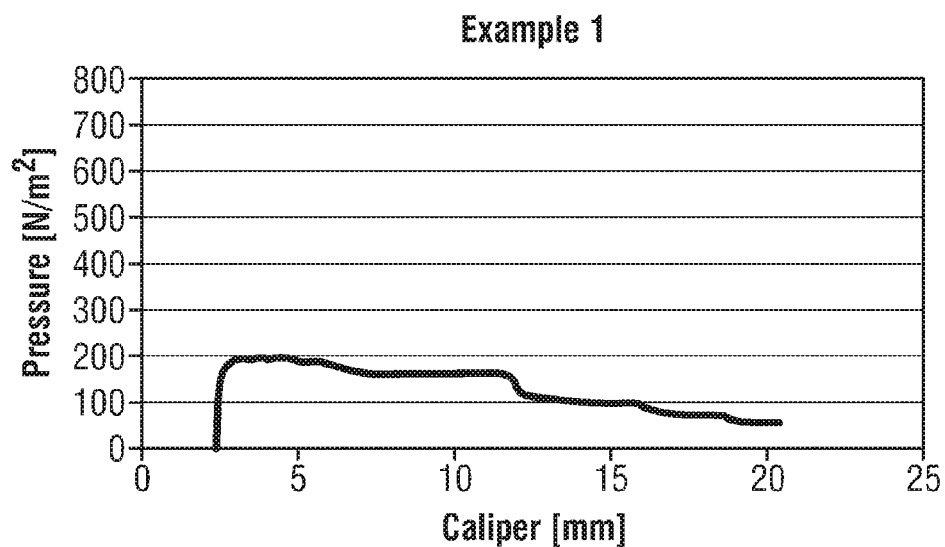
FIG. 6 is a diagram showing pressure versus caliper as measured for Example 1 in the Laminate Compression Extension Test
Figure 7:
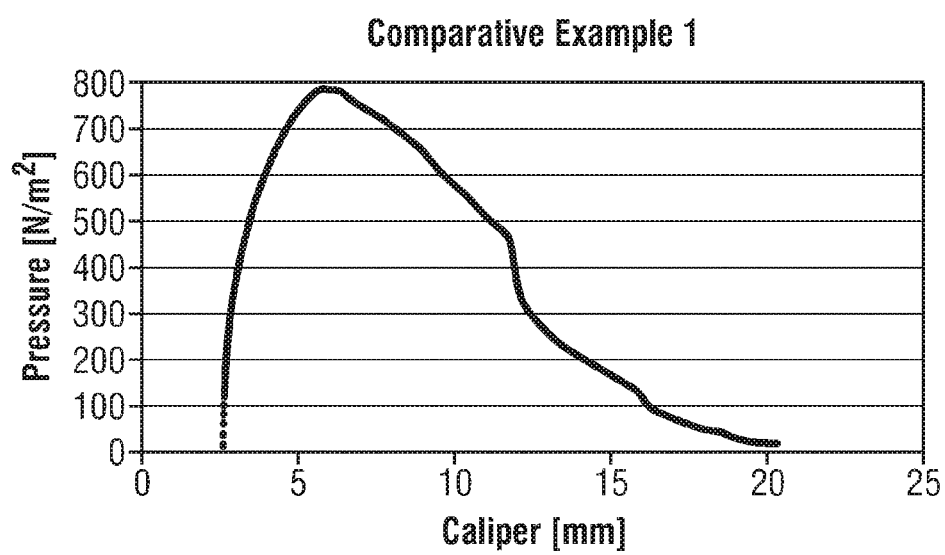
FIG. 7 is a diagram showing pressure versus caliper as measured for Comparative Example 1 in the Laminate Compression Extension Test
Figure 8:
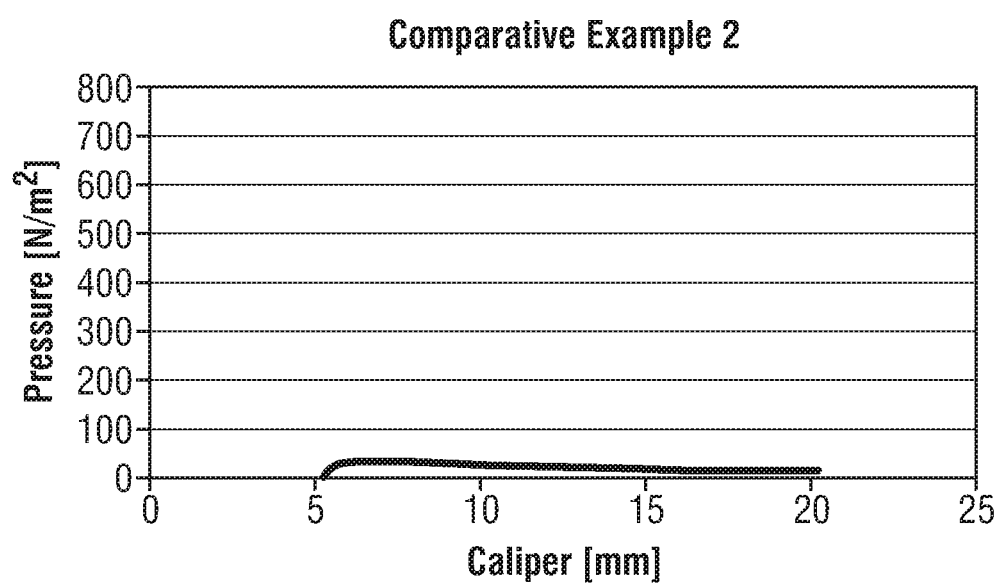
FIG. 8 is a diagram showing pressure versus caliper as measured for Comparative Example 2 in the Laminate Compression Extension Test

Results: Peak Swelling Restriction Pressure and the Swelling Restriction Pressure at 20 mm The diagrams showing the caliper [mm] of the test samples vs. the pressure [N/m$^2$] are depicted in FIGS. 6, 7 and 8.

| | Initial sample caliper [mm] | Peak Swelling Restriction Pressure [N/m$^2$] | Swelling Restriction Pressure at 20 mm [N/m$^2$] | (Peak Pressure)/ (Pressure at 20 mm) |
|---|---|---|---|---|
| Example 1 | 2.5 | 226 | 57 | 4.00 |
| Comparative Example 1 | 2.5 | 788 | 20 | 39.3 |
| Comparative Example 2 | 5.2 | 33 | 12 | 2.79 |

The results show that a laminate absorbent core of Example 1 of the invention has a significantly reduced peak pressure versus the commercially available Comparative Example 1 wherein the superabsorbent polymer material is distributed substantially continuously within the absorbent core.

Also, after separation to 20 mm in the z-direction, the pressure of Example 1 of the invention is significantly higher versus the Comparative Example 1, indicating that considerably lesser delamination within the absorbent core has occurred.

The ratio of Peak Pressure to Pressure at 20 mm is also considerably lower for Example 1 of the invention compared to Comparative Example 1. This reflects that a much more uniform tensile force is needed to separate the laminate layers versus the Comparative Example 1, where a very high peak pressure is followed by a steep drop in the pressure applied when further separating the layers.

Comparative Example 2 shows that in a conventional airfelt-containing absorbent article the force needed to separate the upper carrier substrate from the lower carrier substrate is considerably less compared to a laminate absorbent core having very high amount of superabsorbent polymer material. The absorbent core of Comparative Example 2 is not a laminate absorbent core with two layers. Instead, the absorbent core of Comparative Example 2 comprises a mixture of cellulose fibers and superabsorbent polymer particles, which are encased by nonwoven webs. Hence, the superabsorbent polymer particles are not immobilized by adhesive but are held in place in the interstices between the cellulose fibers. However, the cellulose fibers can be pulled apart in the z-direction of the absorbent core with little forces needed, which is reflected by the data obtained.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A laminate absorbent core comprising a first laminate layer comprising a first substrate layer and superabsorbent polymer particles forming multiple stripes on the first substrate layer and a second laminate layer comprising a second substrate layer and superabsorbent polymer particles forming multiple stripes on the second substrate layer wherein a first adhesive is at least applied between the first laminate layer and the second laminate layer and the superabsorbent polymer particles are immobilized by the first adhesive,
    wherein the stripes of the superabsorbent polymer particles on both the first substrate layer and the second substrate layer are spaced apart from each other to form gaps that are substantially free of superabsorbent polymer particles, wherein the first laminate layer and the second laminate layer are positioned on each other such that the superabsorbent polymer particle stripes of the second laminate layer are overlaying the gaps in the first laminate layer and the superabsorbent polymer particle stripes of the first laminate layer are overlaying the gaps in the second laminate layer and each gap in the first laminate layer is wider than the corresponding superabsorbent polymer particle stripe of the second laminate layer above the gap and each gap in the second laminate layer is wider than the corresponding superabsorbent polymer particle stripe of the first laminate layer below the gap, such that the stripes of superabsorbent polymer particles of the first laminate layer do not contact the stripes of superabsorbent polymer particles of the second laminate layer;
    the superabsorbent polymer particles making up more than 90% by weight of the total amount of material comprised between the first substrate layer and the second substrate layer, wherein the laminate absorbent core has a peak swelling restriction pressure from 50 N/m$^2$ to 400 N/m$^2$, a swelling restriction pressure at 20 mm of more than 30 N/m$^2$, and a ratio of peak swelling restriction pressure to swelling restriction pressure at 20 mm of from 1 to 10.

2. The laminate absorbent core of claim 1, wherein the peak swelling restriction pressure is from 100 N/m$^2$ to 300 N/m$^2$.

3. The laminate absorbent core of claim 1, wherein the swelling restriction pressure at 20 mm is from 30 N/m² to 100 N/m².

4. The laminate absorbent core of claim 1, wherein the laminate absorbent core has a longitudinal direction and a lateral direction, and wherein the stripes of superabsorbent polymer material extend in the longitudinal direction.

5. The laminate absorbent core of claim 1, wherein the laminate absorbent core comprises a second adhesive which is applied on the first and second carrier substrate at least in the gaps formed between neighboring stripes of superabsorbent polymer particles.

6. The laminate absorbent core according to claim 1, the superabsorbent polymer particles make up more than 95% optionally by weight of the total amount of material comprised between the first and second carrier substrates.

7. The laminate absorbent core according to claim 1, wherein the laminate absorbent core comprises less than 5% by weight of cellulose fibers.

8. Absorbent article comprising a topsheet, a backsheet and a laminate absorbent core according to claim 1.

9. The laminate absorbent core according to claim 1, wherein the edge of the superabsorbent polymer particle stripe of the first laminate layer is spaced apart by at least 1 mm from the edge of the superabsorbent polymer particle stripe of the second laminate layer.

10. The laminate absorbent core according to claim 1, wherein the edge of the superabsorbent polymer particle stripe of the first laminate layer is spaced apart by at least 3 mm from the edge of the superabsorbent polymer particle stripe of the second laminate layer.

11. The laminate absorbent core according to claim 1, wherein the edge of the superabsorbent polymer particle stripe of the first laminate layer is spaced apart by less than 10 mm from the edge of the superabsorbent polymer particle stripe of the second laminate layer.

12. The laminate absorbent core according to claim 1, wherein the edge of the superabsorbent polymer particle stripe of the first laminate layer is spaced apart by at less than 5 mm from the edge of the superabsorbent polymer particle stripe of the second laminate layer.

13. The laminate absorbent core according to claim 1, wherein the spacing between the superabsorbent polymer particle stripes of the laminate absorbent core is the same on both sides of the superabsorbent polymer material stripe.

14. The laminate absorbent core according to claim 1, wherein the spacing between the superabsorbent polymer particle stripes of the laminate absorbent core is larger on one side of the superabsorbent polymer material stripe than the other side of the superabsorbent polymer material stripe.

* * * * *